United States Patent [19]
LaSalle et al.

[11] Patent Number: 5,976,147
[45] Date of Patent: Nov. 2, 1999

[54] MODULAR INSTRUMENTATION FOR BONE PREPARATION AND IMPLANT TRIAL REDUCTION OF ORTHOPEDIC IMPLANTS

[75] Inventors: David L. LaSalle, Woonsocket, R.I.; Phillip G. Withee, Attleboro, Mass.; Mark Denney, Medfield, Mass.; George B. Cipolletti, Duxbury, Mass.

[73] Assignee: Johnson & Johnson Professional, Inc, Raynham, Mass.

[21] Appl. No.: 08/890,784

[22] Filed: Jul. 11, 1997

[51] Int. Cl.$^6$ .................................................. A61B 17/56
[52] U.S. Cl. .............................................. 606/88; 606/102
[58] Field of Search .................................. 606/88, 89, 87, 606/86, 96, 97, 98, 102; 623/20, 18

[56] References Cited

U.S. PATENT DOCUMENTS

| | | | |
|---|---|---|---|
| 4,211,228 | 7/1980 | Cloutier | 128/303 |
| 4,736,737 | 4/1988 | Fargie et al. | 128/92 |
| 4,759,350 | 7/1988 | Dunn et al. | 128/92 |
| 4,952,213 | 8/1990 | Bowman et al. | 606/79 |
| 5,275,603 | 1/1994 | Ferrante et al. | 606/86 |
| 5,342,368 | 8/1994 | Petersen | 606/88 |
| 5,356,414 | 10/1994 | Cohen et al. | 606/88 |
| 5,415,662 | 5/1995 | Ferrante et al. | 606/86 |
| 5,431,656 | 7/1995 | Clift, Jr. et al. | 606/86 |
| 5,520,692 | 5/1996 | Ferrante | 606/80 |
| 5,609,642 | 3/1997 | Johnson et al. | 623/20 |
| 5,613,970 | 3/1997 | Houston et al. | 606/88 |
| 5,628,749 | 5/1997 | Vendrely et al. | 606/80 |
| 5,634,927 | 6/1997 | Houston et al. | 606/96 |

OTHER PUBLICATIONS

Johnson & Johnson Orthopaedics, "Primary Cruciate–Retaining Procedure," Specialist 2 Instruments, Surgical Technique for Use with P.F.C.® Knee Systems, pp. 53–55.

Johnson & Johnson Orthopaedics, "Revision Surgery for Failed Total–Knee Replacement,"P.F.C.® Modular Total Knee System with Specialist® Revision Instruments, pp. 10–11.

Johnson & Johnson Orthopaedics, "Specialist® Intramedullary Tibial Alignment System," Surgical Technique, p. 2.

*Primary Examiner*—Guy V. Tucker
*Attorney, Agent, or Firm*—Nutter, McClennen & Fish LLP

[57] ABSTRACT

The invention provides a modular system of components used as bone preparation tools and trial prosthesis components. The system includes a trial tibial tray bearing element that mounts upon a prepared tibia, a punch bushing that serves the purpose of a trial tibial stem and helps to guide a tibial punch through the tibia. The trial template element, the punch bushing and the tibial punch can remain in position on the patient's tibia while one or more trial tibial bearing inserts or samples are attached thereto to determine the proper fit and orientation of a prosthesis.

19 Claims, 6 Drawing Sheets

MODULAR INSTRUMENTATION FOR BONE PREPARATION AND IMPLANT TRIAL REDUCTION OF ORTHOPEDIC IMPLANTS

BACKGROUND OF THE INVENTION

The invention relates to instruments used in bone preparation and implant trial reduction during joint arthroplasty procedures. More particularly, the invention relates to modular instruments used to prepare the tibia to accept a prosthetic tibial tray, and to instruments useful as trial tibial trays.

Joint arthroplasty procedures in which a diseased and/or damaged natural joint is replaced with a joint prosthesis are well known. Among the more common joint arthroplasty procedures are those that involve replacement of knee joints and hip joints.

Knee arthroplasty is a surgical procedure by which a diseased and/or damaged natural knee joint is replaced with a prosthetic knee joint. A typical total knee prosthesis includes a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert. The tibial tray is mounted within the tibia of a patient. Tibial trays typically include a keel or stem extending from the inferior surface thereof. This keel or stem can be implanted within a prepared cavity of the tibia that is formed during the surgical procedure. The tibial tray is secured to the tibia by bone cement and/or by press fit fixation techniques. The tibial bearing insert is typically affixed to the superior surface of the tibial tray.

During the course of a joint arthroplasty procedure, surgeons must evaluate the size and condition of the patient's bones (e.g., the tibia) that will accept a component of the joint prosthesis. In addition, the affected bones must be prepared to receive the prosthesis components. Bone preparation and the choice of the appropriate prosthesis components are factors which significantly influence the success of a joint arthroplasty procedure. Obviously, the bone preparation procedures are tedious and time consuming.

Once a bone has been properly prepared to accept a prosthesis component, surgeons typically utilize a "trial" system of prosthesis components that are provided by the prosthesis manufacturer. The trial components are sample prosthesis components, available in various sizes and shapes, that are intended to be placed into the prepared bone on a temporary basis for evaluation purposes only. Typically, surgeons evaluate a number of different trial components to determine the size and/or shape of a prosthesis component that will best suit a patient's needs.

In many joint arthroplasty procedures separate sets of tools and components are used to prepare the bone and subsequently to evaluate various prosthesis trial components. The use of separate sets of tools and components for these steps in a joint arthroplasty procedure further complicates an already difficult and time consuming process. Many prior art techniques require the removal of all bone preparation components after the bone has been prepared. Subsequently, the trial components are then sampled within the prepared bone.

U.S. Pat. No. 5,628,749 discloses instrumentation useful to prepare the proximal tibia to accept a tibial prosthesis. This instrumentation enables a surgeon to effect all necessary resection and drilling of the femur. When this is accomplished, a tibial trial is placed on the prepared tibia for evaluation of size and fit. Other instruments useful for preparation of the proximal tibia are disclosed in U.S. Pat. No. 4,759,350.

U.S. Pat. No. 5,609,642 discloses a tibial trial and bone preparation system. This system enables a surgeon to place a tibial tray trial on a resected tibia, and to rotate the tray trial to a preferred position. When the preferred position is achieved femoral and tibial trials are allowed to articulate with each other through the full range of motion of the knee. The trial tibial bearing insert is then removed from the trial tibial tray and the tibia is further prepared using a fin punch.

SUMMARY OF THE INVENTION

The invention is directed to a modular system that is used during the bone preparation and trial reduction phases of joint arthroplasty surgery. In particular, the system is particularly applicable to modular instruments for preparation of the proximal tibia, and to trial components for the tibial tray and the tibial bearing insert.

The system of the invention includes a trial tibial tray template element that serves both as a template, or guide, during preparation of the tibia and as a tibial tray trial element during the fitting of a tibial bearing insert. The tibial tray trial element has a superior surface and a bone contacting inferior surface. At least one guide aperture extends through the element from the superior to the inferior surfaces thereof. Further, the trial tibial tray template element preferably includes at least one locking aperture, and preferably at least two locking apertures, that are positioned on the opposite sides of the guide aperture and which extend through the superior and inferior surfaces of the element. One or more slots may extend radially from the central aperture.

The system also includes at least one punch bushing that is selectively mateable with the trial tibial template element. The punch bushing serves both as the guide or template during the bone preparation procedures, and also as a trial element that remains mounted within the patient's tibia during the trial portion of the surgical procedure. The punch bushing is an elongate member that has proximal and distal ends. A proximal end of the punch bushing includes a collar that is sized and configured to mate, in a clearance fit, with the guide aperture of the trial tibial tray template element. The punch bushing extends distally from the collar such that the diameter of the bushing generally tapers from proximal to distal ends thereof. The distal end is adapted and configured to mate with a prepared cavity within the patient's tibia and, accordingly, it assumes the size and shape of the distal portion of a permanent tibial tray prosthesis. The punch bushing further includes a central bore that extends at least partially into the bushing from the proximal surface of the collar. Further, at least two opposed slots extend radially from the central bore at least partially into the bushing.

The system also includes at least one tibial punch that is insertable within the bore and the slots of the punch bushing to create a further opening within the patient's tibia of a size and shape that is complimentary to the tibial punch. The tibial punch has a central hub with proximal and distal ends. Wedge-like fins extend radially from the central hub and are tapered in width from proximal to distal ends thereof. The outer edges of the wedge-like element preferably are bone penetrating. The punch is of a size and shape such that it is able to fit within the bore and slots of the punch bushing. A proximal end of the tibial punch includes a connecting surface that has a top, impact surface that can be used to hammer the tibial punch into the tibia.

The system also includes a selection of trial tibial bearing inserts, each of which has a superior articulation surface and an inferior surface that includes a mating aperture. The mating aperture is configured to selectively mate with the connecting surface of the tibial punch.

The system of the invention is useful in the following manner. The trial tibial tray template element is secured to a proximal portion of a patient's tibia, which previously may have been prepared by a resection procedure. A drill bushing can then be joined to the superior surface of the element and, using a suitable bone drill operated through the drill bushing, a cavity of desired dimensions is formed within the patient's tibia. The drill and drill bushing are removed and the punch bushing is inserted into the cavity while allowing the collar of the punch bushing to mate with the guide aperture of the trial tibial tray template element. Next, the tibial punch is inserted within the punch bushing, in the proper orientation, and it is forced, for example by use of a mallet, through the punch bushing and into the tibia to alter the shape of the cavity such that it is complementary to that of the tibial punch. The tibial punch remains in place, together with the trial tibial tray template element and the punch bushing. The surgeon can then attach one or more trial tibial bearing inserts to the connecting surface of the tibial punch to evaluate the size, shape and orientation of a tibial bearing insert needed for a given patient.

DETAILED DESCRIPTION OF THE INVENTION

Figure 1:
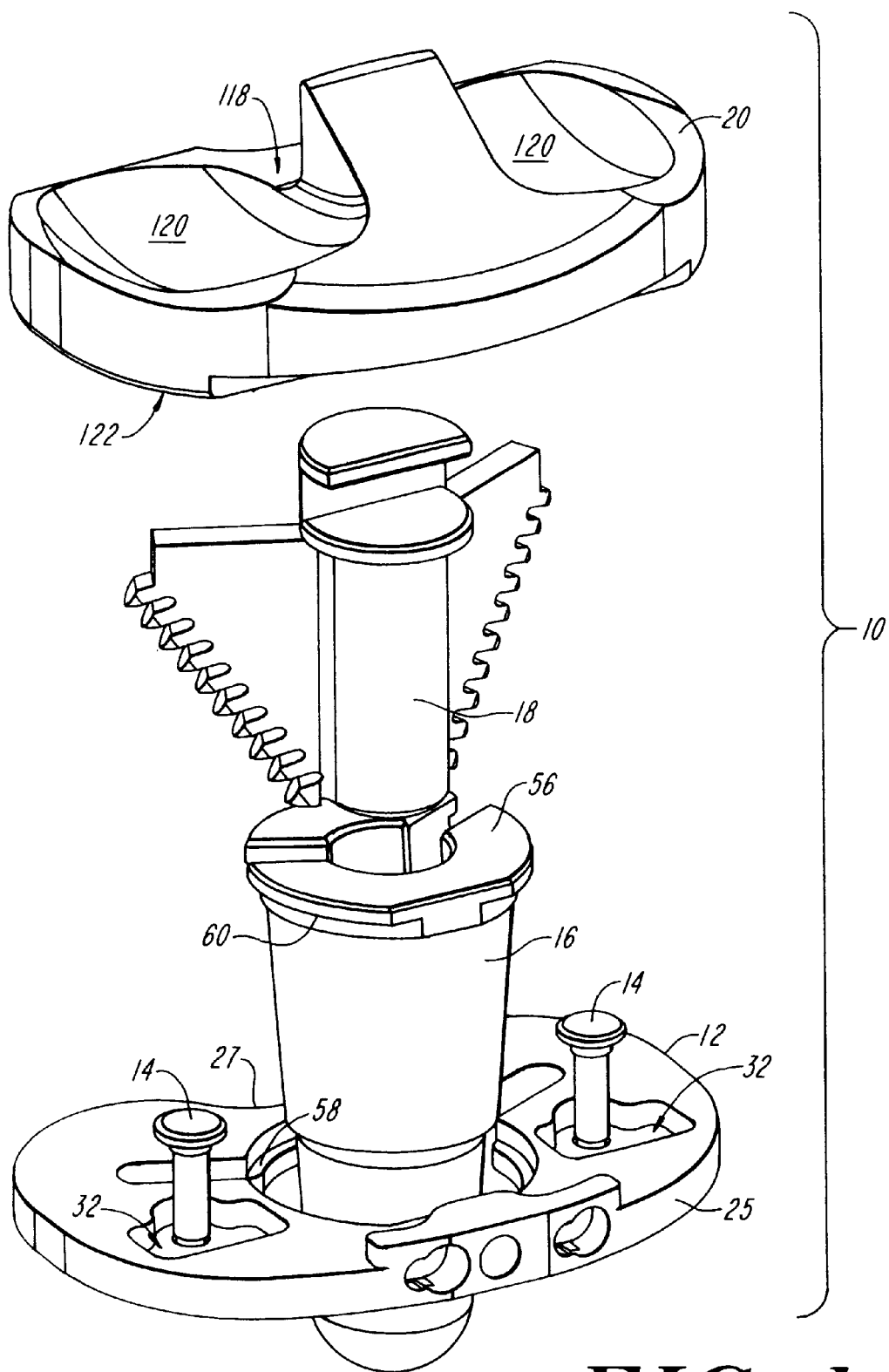
FIG. 1 is an exploded, perspective view of components of the system of the invention.
Figure 2:
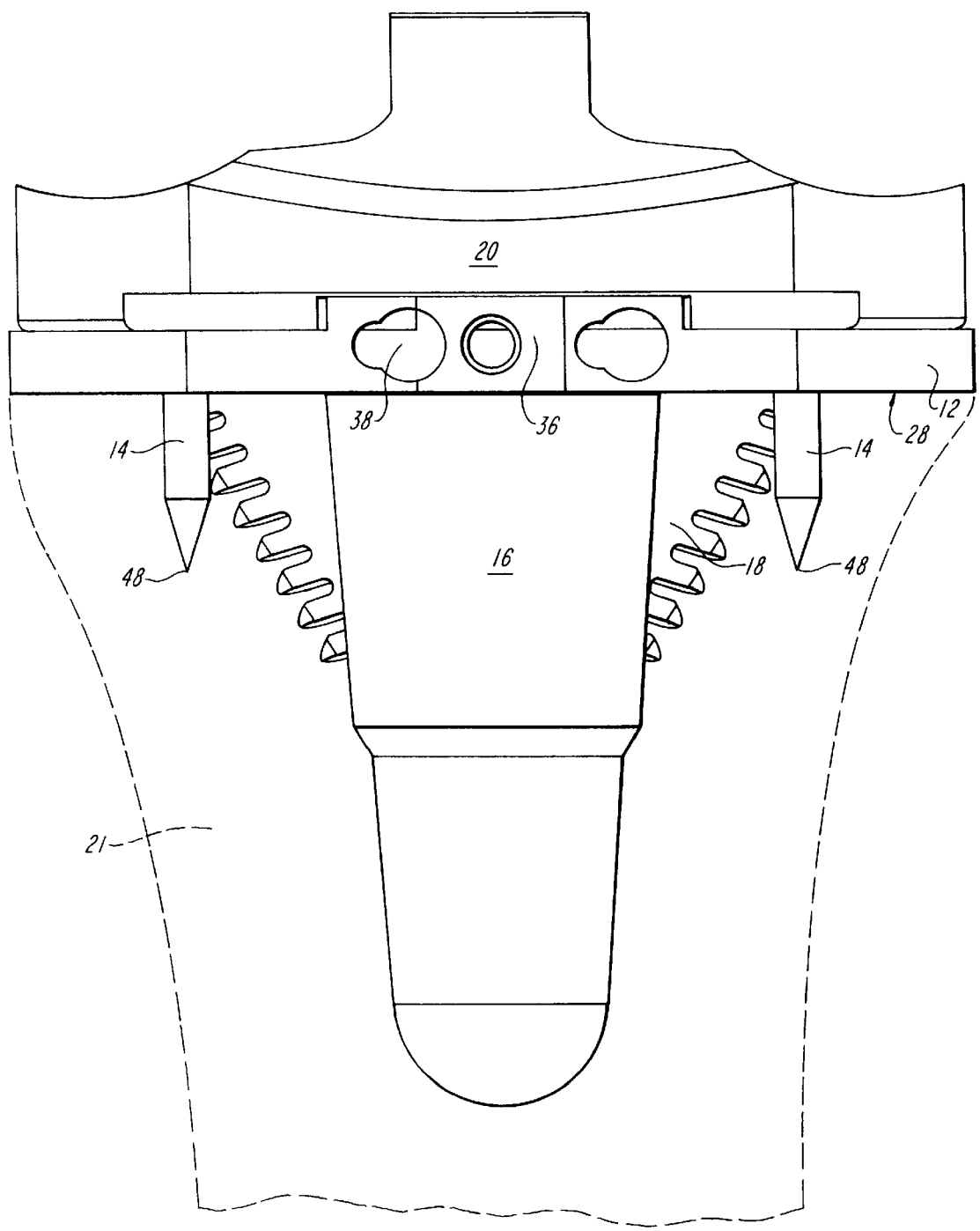
FIG. 2 is an isometric view of the system of the invention, assembled and mounted upon a tibia that is shown in phantom.
Figure 3:
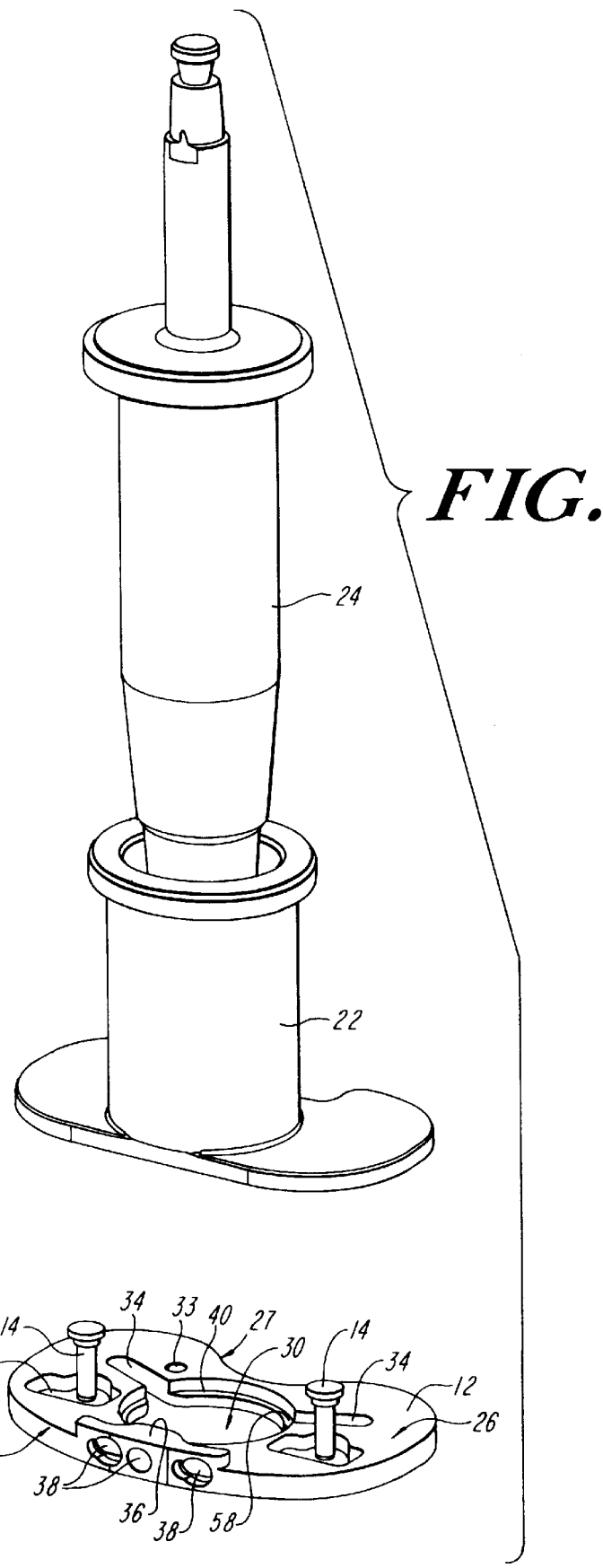
FIG. 3 illustrates an exploded perspective view of the trial tibial tray template element of the system together with a drill bushing and a bone drill bit.
Figure 4:
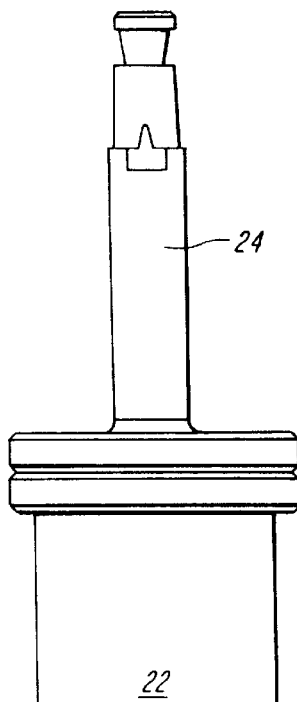
FIG. 4 is an isometric view of a portion of the system of the invention illustrating the trial tibial tray template element mounted to a tibia, shown in phantom, with the drill bushing mounted to the element and a bone drill adjacent to the drill bushing.
Figure 4:
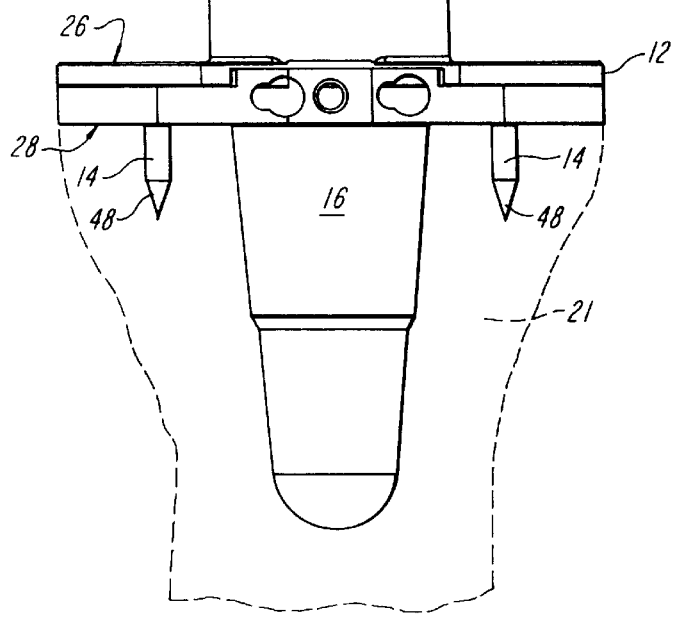

As shown in FIGS. 1 and 3 the modular bone preparation and trial system of the invention comprises various components that are useful to prepare the bone to receive a joint prothesis and also to evaluate the fit of various prosthesis components. These components include a trial tibial tray template element 12, punch bushing 16, tibial punch 18 and trial tibial bearing insert member 20. The system may optionally include a drill bushing 22 and a drill member 24, as shown in FIG. 3.

Referring to FIGS. 1 through 4 and 8, the trial tibial tray template element 12 has a superior surface 26 and an inferior surface 28, and anterior and posterior sides 25, 27. A guide aperture 30 is substantially centrally disposed on the element 12 and extends through the superior and inferior surfaces 26, 28 thereof. The trial tibial tray template element 12 preferably includes locking apertures 32 which may be disposed on opposite sides of the central aperture 30. In addition, at least two slots 34 extend radially, and preferably posteriorly, from the guide aperture 30. Slots 34 extend through the superior and inferior surfaces 26, 28 of element 12. Optionally, the trial tibial tray template element 12 includes an anterior flange 36 that is slightly raised above the superior surface 26 of the element 12. Anterior flange 36 includes one or more apertures 38. Flange 36 and apertures 38 provide a mechanism to cooperate with a handle (not shown) used to manipulate and move the element 12.

The guide aperture 30 may be substantially circular. In a preferred embodiment, however, the guide aperture 30 is substantially D-shaped and includes a perimeter having an arc portion 40 and a flat, non-arc portion 42. The D-shaped perimeter of the guide aperture is intended to help properly position and lock other components within the guide aperture 30, and it is understood that other profiles, besides D-shaped, may be employed. Further, in a preferred embodiment the non-arc portion 42 of the perimeter is adjacent an anterior side 25 of the trial element 12, but it is understood that this non-arc segment may be located at other portions of the perimeter.

The nominal diameter ($D_{m-l}$) of the guide aperture 30, measured in the medial-lateral plane, is in the range of about 1.0 to 1.30 inches. Likewise, the nominal diameter ($D_{a-p}$) of the guide aperture 30, measured in the anterior-posterior plane, is in the range of about 0.80 to 1.20 inches. One of the ordinary skill in the act will appreciate that the diameter of the guide aperture 30 may be lesser or greater than the values noted above.

As noted above, slots 34 extend radially from a portion of the guide aperture 30. Although preferred, it is not necessary that the trial tibial tray template element 12 include slots 34. However, when present, the slots should be of a length of approximately 1.00 to 1.50 inches and a width of about 0.15 to 0.38 inch. The slots 34 should extend completely through the template element 12 from the superior surface 26 to the inferior surface 28. The slots 34 may extend at any desired angular orientation from the guide aperture 34. In a preferred embodiment, however, the slots 34 are posteriorly directed and extend at an angle relative the transverse axis 46 of between 0 and 75 degrees in the posterior direction. In one embodiment, the slots 34 extend at an angle of between about 30 and 60 degrees, and most preferably at an angle of about 45 degrees. In another embodiment the angle formed by the slots 34 with the transverse axis 46 is 0 degrees. It is further understood that each of the slots 34 may extend at a different angle relative to transverse axis 46.

The trial tibial tray template element 12 preferably includes one or more locking apertures 32 that are used to affix the elements 12 to the tibia when the element 12 is properly positioned. A locking mechanism, such as bone penetrating pins 14, cooperates with the locking apertures 32 to affix the element 12 to the tibia. In a preferred embodiment the pins 14 are elongate bone pins that are driven into the tibia to secure the elements 12 in position. Locking pins 14 preferably have a length in the range of about 10 to 25 mm and include a bone penetrating distal end 48.

FIGS. 1, 2, 4 and 9–12 illustrate the punch bushing 16, which is an elongate member having proximal and distal ends 50, 52. The proximal end 50 preferably includes a collar 54 that is of a size and shape complementary to guide aperture 30. Preferably, the collar 54 is sized to fit within guide aperture in a clearance fit such that a superior surface 56 of the collar 54 mounts in a manner such that it is slightly recessed or flush with respect to superior surface 26 of trial element 12. In a preferred embodiment the guide aperture 30 includes a shoulder 58 that supports an inferior surface 60 of the collar 56 to ensure that the superior surface of the collar 54 is slightly recessed with respect to superior surface 26 of element 12.

In a preferred embodiment the collar 54 is substantially D-shaped having a perimeter with an arc portion 62 and a flat non-arc portion 64.

The proximal end 50 and collar 54 of punch bushing 16 preferably include a central bore 68 that may be substantially circular in shape. The bore 68 extends at least partially into bushing 16. The bore 68 may have a diameter that is substantially constant along its entire length, or the diameter may vary with the depth of the bore. In one embodiment, illustrated in FIG. 11, the bore has a substantially constant first diameter region 69 that extends over a majority of its length. Region 69 terminates in a restricted diameter region 70 that extends to the distal end 72 of the bore.

Slots 35 preferably extend radially from bore 68. The slots 35 are intended to cooperate with slots 34 of trial element 12 to form a guide for the wedge-like fins 63 of tibial punch 18. As such, the size and orientation of slots 35 should be as described above for slots 34.

Preferably, slots 35 extend radially and posteriorly from the bore 68. The angle formed by each slot with the transverse axis 46 of the punch bushing 16 is in the range of about 0° to 75° in the posterior direction. Preferably, the slots 35 extend at an angle from about 30° to 60°, and most preferably at an angle of about 45°. The slots 35 should have a length of about 5 to 50 mm and a width of about 2 to 8 mm. Preferably the slots 35 extend within the bore 68 to a depth of about 25 mm.

The depth and diameter of the bore 68 may vary depending upon the requirements of a given application. Generally, the bore should be sized and shaped so as to accept the tibial punch, as described below. In an exemplary embodiment, however, the diameter of the bore is in the range of about 0.40 to 1.20 inches. In a preferred embodiment, illustrated in FIG. 11, the diameter in region 69 is from about 0.80 to 1.00 inch. The length of the region 69 is about 1.2 to 2.0 inches. Further, the diameter of region 70 tapers at an angle of about 30° to 50° from about 0.70 to 0.50 inch. The length of region 70 is about 0.30 to 0.70 inch.

Figure 9:
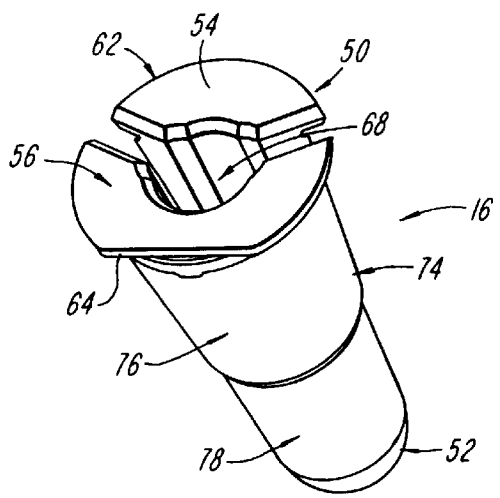
FIG. 9 is a perspective view of a punch bushing of the system.
Figure 10:
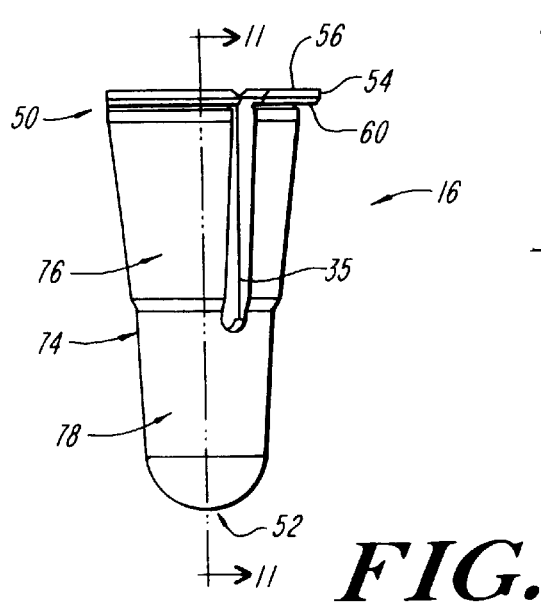
FIG. 10 is a side view of the punch bushing FIG. 9.
Figure 11:
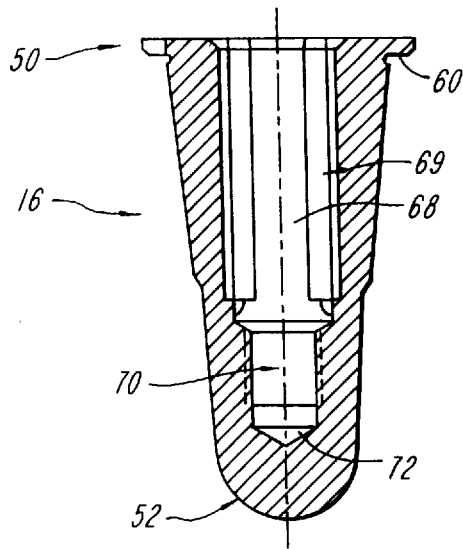
FIG. 11 is a sectional view at lines 11—11 of the punch bushing shown in FIG. 10.
Figure 12:
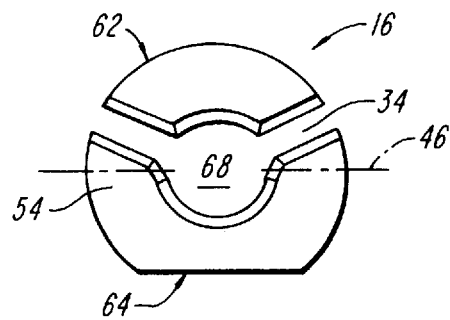
FIG. 12 is a top view of the punch bushing of FIG. 9.

With further reference to FIGS. 9 through 11, the punch bushing 16 includes an outer surface 74. The outer surface 74 is intended to be implanted within the tibia to form a bone-contacting surface. The distal end 52 of punch bushing 16 preferably is spherical. The size and shape of the outer surface of punch bushing may vary depending upon the requirements of a given application. Generally, however, it is understood that the distal end 52 is intended to serve the purpose of a tibial stem prosthesis. Accordingly, it should be of a size and shape consistent with that desired for the distal portion of a permanent tibial tray prosthesis.

In one embodiment, the outer surface has a first region 76 that is disposed distally of the collar. A second region 78 is formed distally of the first region. Preferably, the first region 76 has a diameter that tapers from a widest portion, at a proximal end of first region, to a narrowest portion at the distal-most end of the first region. Preferably, the diameter of the widest portion of the first region 76 is approximately 0.90 to 1.00 inch. The taper of the first region 76 preferably extends at an angle of about 5 degrees to 6 degrees, and most preferably about 5.75 degrees. Similarly, the diameter at the widest, most proximal portion of the second region 78 is in the range of about 0.60 to 0.70 inch, and most preferably is about 0.68 to 0.69 inch. In one embodiment the length of the first region 76 is approximately 1.0 to 1.2 inch while the length of the second region 78 is about 2.00 to 2.10 inch.

The tibial punch 18 is a substantially wedged-shaped member that is inserted through the punch bushing 16 and into a patient's tibia 21 to form an opening in the bone that will be of a suitable size and shape to receive the fin elements of a prosthetic tibial tray (not shown). The tibial punch includes a hub 80 that is substantially elongate and cylindrical. Two wedge-like fins 63, which extend from opposite sides of the central hub 80, have a width that tapers from proximal to distal ends 82, 84 thereof. In addition, the outer edges 86 of the wedge-like fins are of a shape and/or configuration to facilitate bone penetration. In one embodiment the outer edges are serrated.

A proximal end 88 of the tibial punch 18 includes a connecting element 90 that will protrude above the superior surface of trial element 12 when the system is fully assembled. The connecting element 90 preferably includes a base surface 92 that is normally horizontally oriented. The base surface 92 is separated from a top surface 94 by a vertical connecting surface 96. The top surface 94 is preferably horizontal. The connecting element 90 is configured to mate with a universal handle (not shown) which can receive blows from a mallet (not shown) while the punch 18 is being forced into a patient's tibia. The space between the base surface 92 and the top surface 94 forms a lip 100 that can be used to engage or mate with a trial tibial bearing insert 20, as described below.

The size and shape of the tibial punch 18 should be such that it is able to fit within the bore 68 and slots 35 of the punch bushing 16 in a clearance fit. That is, the cylindrical hub 80 should be of substantially the same shape and a slightly smaller diameter than the bore 68 of the punch bushing 16. Similarly, the wedge-like fins 63 should extend from the hub 80 at substantially the same angle as do the slots extend from the bore of the punch bushing 16. Thus, the wedge-like fins 63 extend from the hub 80 at an angle, relative to the transverse axis 46, of between 0 and 75 degrees. In one embodiment the angle formed by fins 63 with the transverse axis 46 is from about 30 to 60 degrees, and most preferably, about 45 degrees. In another embodiment the angle formed by fins 63 with transverse axis 46 is 0 degrees. It is further understood that each of the fins 63 may extend at a different angle relative to transverse axis 46.

As noted above, the width of fins 63 tapers from the proximal to the distal ends 82, 84 of the tibial punch. The taper angle $\alpha$ can vary, but it preferably is in the range of about 50° to 65°. The width of the punch, at its widest point (measured from opposite edges of fins 63) is about 1.85 inches. The width tapers to about 0.65 inch at the narrowest portion of the tibial punch.

Figure 5:
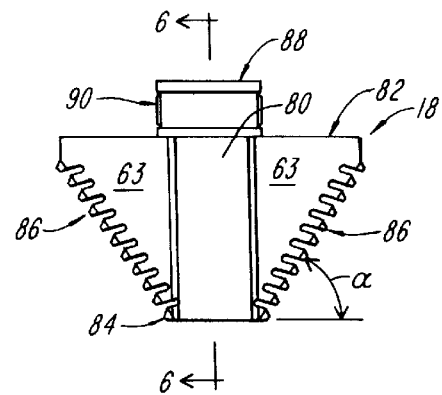
FIG. 5 is an anterior view of the tibial punch.
Figure 6:
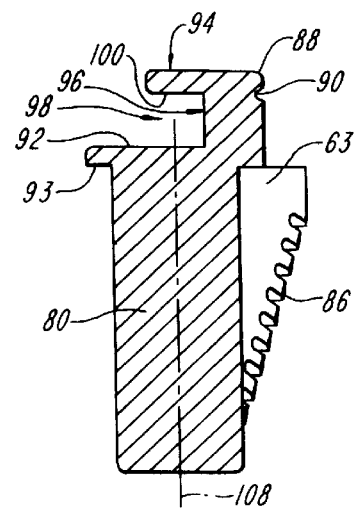
FIG. 6 is a side sectional view of the tibial punch shown in FIG. 5, at lines 6—6.
Figure 7:
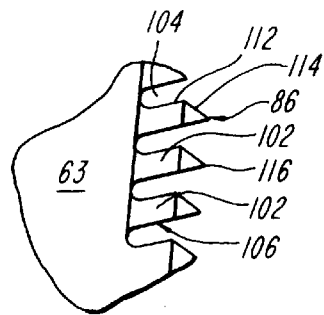
FIG. 7 is a detailed view of a portion of the wedge-like element of the tibial punch shown in FIG. 5.
Figure 8:
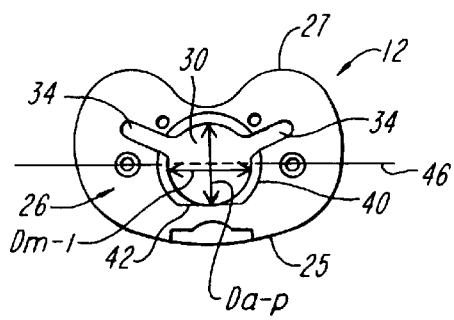
FIG. 8 is a top view of the trial tibial tray template element of the system.

As noted above, the outer edges 86 of the wedge-like fins 63 may be serrated. FIGS. 5 through 7 illustrate one embodiment in which the outer edges 86 form bone penetrating teeth 102. As illustrated, each tooth 102 is separated from an adjacent tooth by a space 104. Further, each tooth 102 has a base, or distal, surface 106 that is oriented at an angle of approximately 65 degrees relative to the longitudinal axis 108 of the punch 18. The proximal surface 110 of each tooth includes a first component 112 that is substantially parallel to the base surface 106 and a canted face 114 which meets the base surface 106 at apex 116. The canted face 114 forms an angle of approximately 45 degrees with the base surface 106.

The trial tibial bearing member 20 is of a type that is known in the art to be useful for evaluating the fit of a prosthesis. Typically, the system 10 includes one or more of the trial tibial bearing members 20 in various sizes and orientations.

Figure 13:
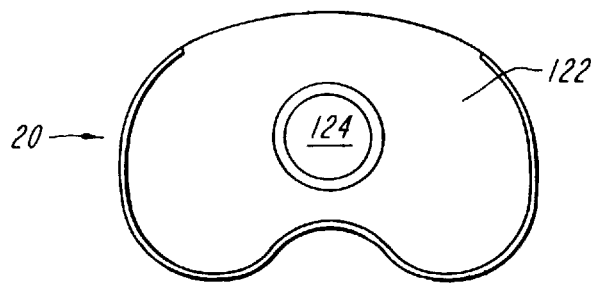
FIG. 13 is a bottom view of a representative trial tibial bearing insert of the system of the invention.

The trial tibial bearing insert 20 includes a superior articulation surface 118 which may have one or more condylar elements 120. As shown in FIG. 13, an inferior surface 122, which is adapted to mate with the connecting surface of the tibial punch, rests on superior surface of the trial tibial tray template element 12 when the system is fully assembled. Inferior surface 122 preferably includes a mating aperture 124 that is adapted to house the connecting surface of the tibial punch removably and replaceably mate to bearing insert 20 to the rest of the system.

The system 10 of the invention is used in the following manner. The proximal surface of a tibia 21 is resected in a known manner and the trial element 12 is then properly positioned on the resected tibia and secured in place on a tibia by the locking pins 14. The drill bushing 22 is then attached to the trial element 12 by mating dowel pins (not shown) on an inferior surface of drill bushing 22 with holes 33 of element 12, and then drill element 24 is inserted through the bushing 22 and used to form a cavity of a desired depth and diameter within the tibia 21. Once the cavity is formed the drill element 24 and drill bushing 22 are removed. The punch bushing 16 is then mounted upon trial element 12 such that the distal end 52 of the punch bushing 16 is inserted into the cavity within the tibia and the collar 54 mounts within the guide aperture 30 of trial element 12. The tibial punch 18 is then inserted into the bore 68 and slots 35 of the guide bushing 16 and is forced into the tibia (e.g., by hammering) until the underside 93 of base surface 92 contacts the superior surface 56 of collar 54.

The components of the system used to prepare the bone (e.g., the punch bushing and the tibial punch) remain in place once the bone has been prepared and, together with trial element 12 and trial tibial bearing element 20, serve as components of the trial system. Once the tibial punch 18 is properly positioned it is left in place, as noted above, and a surgeon can attach one or more trial tibial bearing elements 20 to the connecting surface 90 so as to form a full trial tibial prosthesis. The size and fit of the various trial tibial bearing inserts are evaluated and the surgeon determines the proper components to use in a prosthetic joint, and the proper orientation of such components. Thereafter, the components of the system are removed and are replaced with permanent prosthesis components in a manner known in the art.

It is understood that various modifications can be made to the present invention without departing from the intended scope thereof. The entirety of all references noted herein is expressly incorporated by reference herein.

What is claimed is:

1. A bone preparation and trial system, comprising:
    at least one trial tibial tray template element having a superior surface and a bone-contacting inferior surface with at least one guide aperture extending through the element from the superior to the inferior surfaces thereof;
    at least one locking aperture formed in the trial tibial tray template element;
    at least one punch bushing in the form of an elongate member selectively matable within the at least one guide aperture of the trial tibial tray template element, the punch bushing having a distal end adapted to mate within a patient's tibia and a proximal end having a collar matable with the guide aperture, the collar including a centrally disposed bore extending at least partially into the punch bushing and a pair of opposed slots, each opposed slot extending radially from the bore and extending at least partially into the punch bushing;
    at least one tibial punch insertable within the bore and slots of the punch bushing to create an opening within the patient's tibia of a size and shape complementary to the tibial punch, the tibial punch having distal and proximal ends wherein
        a wedge-like member, formed on the distal end thereof, includes opposed fins with bone-penetrating outer surfaces, the opposed fins being adapted for mating within the slots of the punch bushing, and
        a connecting element, formed on the proximal end thereof; and
    at least one trial tibial bearing insert, each trial tibial bearing insert having a superior articulation surface and an inferior mating surface adapted to mount upon the superior surface of the trial tibial tray template element, the inferior mating surface further including a mating aperture matable with the connecting element of the tibial punch.

2. The system of claim 1 wherein the guide aperture is substantially round.

3. The system of claim 1 wherein the aperture is substantially D-shaped, having an arc portion and a flat, non-arc portion.

4. The system of claim 3 wherein the flat, non-arc portion is disposed adjacent an anterior portion of the trial tibial tray template element.

5. The system of claim 3 wherein the collar of the punch bushing is substantially D-shaped and is sized to fit within the guide aperture in a clearance fit such that in a fully mated position a superior surface of the collar is slightly recessed with respect to the superior surface of the trial tibial tray template element.

6. The system of claim 1 wherein the guide aperture has a nominal diameter, measured in the medial-lateral plane, in the range of about 1.00 to 1.30 inches.

7. The system of claim 1 wherein the guide aperture has a nominal diameter, measured in the anterior-posterior plane, in the range of about 0.80 to 1.20 inches.

8. The system of claim 1 wherein the locking apertures are formed on opposite sides of the guide aperture.

9. The system of claim 8, further comprising a plurality of locking pins removably insertable within the locking aperture to selectively secure the trial tibial tray template element to a patient's tibia.

10. The system of claim 1 wherein the slots of the punch bushing extend at an angle of 0° with respect to a transverse axis of the punch bushing.

11. The system of claim 1 wherein the slots of the punch bushing extend posteriorly.

12. The system of claim 11 wherein the slots form an angle with respect to the transverse axis of the trial tibial tray template element in the range of about 30° to 60°.

13. The system of claim 11 wherein the length of each slot is about 1.00 to 1.50 inches.

14. The system of claim 1 wherein the bone-penetrating outer surfaces of the wedge-like member are serrated.

15. The system of claim 1, wherein the connecting element comprises
a base portion;
a vertical connecting wall to oriented transversely to the base portion; and
a top surface appended to the vertical connecting well and spaced apart from the base portion.

16. The system of claim 1 further comprising a drill bushing removably mountable upon the superior surface of the trial tibial tray template element.

17. A bone preparation and trial system, comprising:
at least one trial tibial tray template element having a superior surface and a bone-contacting inferior surface with at least one guide aperture extending through the element from the superior to the inferior surfaces thereof, the guide aperture including a pair of opposed slots extending radially from the guide aperture;
locking means for selectively securing the trial tibial tray template element to a patient's tibia;
at least one punch bushing in the form of an elongate member having proximal end that includes a mating collar and a distal end, the mating collar being selectively matable within the at least one guide aperture of the trial tibial tray template element, and the distal end being adapted to mate within a patient's tibia, the punch bushing further including a centrally disposed bore and a pair of opposed slots extending radially from the bore, each of the bore and the slots extending distally from the collar at least partially into the punch bushing;
at least one tibial punch having a central hub with opposed fins extending radially therefrom, each opposed fin tapering in width from a proximal end to a distal end, the central hub and the opposed fins being sized and oriented to be selectively insertable within the bore and slots of the punch bushing to create an opening within the patient's tibia of a size and shape complementary to the tibial punch, the central hub further including a connecting element formed on the proximal end thereof and having a top, impact surface; and
at least one trial tibial bearing insert, each trial tibial bearing insert having a superior articulation surface and an inferior mating surface that is adapted to mount upon the superior surface of the trial tibial tray template element, the inferior mating surface further including a mating aperture matable with the connecting element of the tibial punch.

18. The system of claim 17 wherein the punch bushing tapers in diameter from the collar to the distal end thereof.

19. A method for using a modular, dual purpose bone preparation and prosthesis trial system for a joint arthroplasty procedure, comprising the steps of:
providing a trial tibial tray template element having a superior surface and a bone-contacting inferior surface with at least one guide aperture extending through the element from the superior to the inferior surfaces thereof;
affixing the trial tibial tray template element to a patient's tibia;
attaching a drill bushing to the superior surface of the element and using the drill bushing as a guide to drill a cavity within the tibia;
removing the drill bushing;
providing a punch bushing in the form of an elongate member having proximal end that includes a mating collar and a distal end, the punch bushing further including a centrally disposed bore and a pair of opposed slots extending radially from the bore, each of the bore and the slots extending distally from the collar at least partially into the punch bushing;
mating the punch bushing to the element such that the collar mates with the guide aperture and the distal portion of the punch bushing extends within the cavity formed in the tibia;
providing a tibial punch having a central hub with opposed fins extending radially therefrom, each opposed fin tapering in width from a proximal end to a distal end, the central hub and the opposed fins being sized and oriented to be selectively insertable within the bore and slots of the punch bushing, the central hub further including a connecting element formed on the proximal end thereof and having a top surface;
inserting the tibial punch within the punch bushing to remove bone from the tibia such that a further cavity is created having a size and shape complementary to that of the tibial punch;
allowing the tibial punch, the trial tibial tray template element and the punch bushing to remain in place;
providing at least one tibial bearing insert trial;
attaching, sequentially, for purposes of fit and size evaluation, one or more of the trial tibial bearing inserts to the trial tibial tray template element by joining a mating aperture formed on an inferior surface of the tibial bearing insert trial to the connecting surface of the punch bushing.

* * * * *